(12) United States Patent
Utsuzawa et al.

(10) Patent No.: US 10,408,898 B2
(45) Date of Patent: Sep. 10, 2019

(54) OPTIMIZATION OF MAGNET ARRANGEMENT FOR NUCLEAR MAGNETIC RESONANCE WELL LOGGING TOOLS

(71) Applicant: Schlumberger Technology Corporation, Sugar Land, TX (US)

(72) Inventors: Shin Utsuzawa, Missouri City, TX (US); Anatoly Dementyev, Sugar Land, TX (US); Nicholas Heaton, Houston, TX (US); Cole Mann, Sugar Land, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 548 days.

(21) Appl. No.: 15/087,675

(22) Filed: Mar. 31, 2016

(65) Prior Publication Data
US 2017/0285120 A1 Oct. 5, 2017

(51) Int. Cl.
| | |
|---|---|
| G01R 33/38 | (2006.01) |
| G01V 13/00 | (2006.01) |
| G01V 3/32 | (2006.01) |
| G01N 24/08 | (2006.01) |
| G01R 33/383 | (2006.01) |

(52) U.S. Cl.
CPC ....... *G01R 33/3802* (2013.01); *G01N 24/081* (2013.01); *G01R 33/383* (2013.01); *G01R 33/3808* (2013.01); *G01V 13/00* (2013.01); *G01V 3/32* (2013.01)

(58) Field of Classification Search
CPC ............ G01R 33/0052; G01R 33/3802; G01R 33/3808; G01R 33/383; G01R 33/387; G01R 33/44; G01V 3/32; G01V 13/00; G01N 24/08; G01N 24/081
See application file for complete search history.

(56) References Cited

U.S. PATENT DOCUMENTS

| | | | |
|---|---|---|---|
| 2008/0018334 A1* | 1/2008 | Reiderman | E21B 47/0905 324/346 |
| 2014/0117984 A1 | 5/2014 | Conrad et al. | |
| 2017/0276749 A1* | 9/2017 | Hugon | G01R 33/383 |

OTHER PUBLICATIONS

Soltner, H. et al., "Dipolar Halbach Magnet Stacks Made from Identically Shaped Permanent Magnets for Magnetic Resonance", Concepts in Magnetic Resonance Part A, 2010, 36A(4), pp. 211-222.

* cited by examiner

*Primary Examiner* — Peter Dungba Vo
*Assistant Examiner* — Joshua D Anderson (57) ABSTRACT

A method to produce a magnet arrangement, the method having steps of selecting a depth of investigation to be achieved by a downhole tool, identifying a desired magnetic field strength at the depth of investigation, producing a set of magnets to be incorporated into the downhole tool, sorting the set of magnets based on a quality of each of the magnets and optimizing the set of magnets such that the quality of each of the magnets results, when arranged, in the desired magnetic field strength at the depth of investigation and wherein the optimizing minimizes a cost function of the set of magnets produced.

10 Claims, 7 Drawing Sheets
(6 of 7 Drawing Sheet(s) Filed in Color)

OPTIMIZATION OF MAGNET ARRANGEMENT FOR NUCLEAR MAGNETIC RESONANCE WELL LOGGING TOOLS

CROSS-REFERENCE TO RELATED APPLICATIONS

None.

FIELD OF THE INVENTION

Aspects described relate to nuclear magnetic resonance well logging tools. More specifically, aspects described relate to optimization of magnetic arrangements for nuclear magnetic resonance well logging tools to reduce waste and increase economic production and output of such arrangements.

BACKGROUND INFORMATION

Nuclear magnetic resonance well logging tools are vitally important to oil field service companies in efforts to obtain extraction of hydrocarbons from geological stratum. Nuclear magnetic resonance well logging tools use specially made arrangement magnets to investigate the geological stratum to desired operating conditions. As a result, different well logging tools may be used if there are different desired depths of investigation.

Nuclear magnetic resonance well logging tools are expensive to produce, however it is important to produce these well logging tools at an economical total cost. One of the most significant aspects of the cost of nuclear magnetic resonance well logging tools is creation and arrangement of magnets in the tool. Reduction of the waste resulting from magnet creation provides significant cost savings.

Placement of magnets in a nuclear magnetic resonance well logging tool is conventionally performed using specially designed magnets. These magnets, however, are not optimal in their overall performance. As a result, static magnetic field ($B_0$) produced by conventional, well logging tools deviates from the original design. This imperfect magnetic field distribution may produce a distorted nuclear magnetic resonance signature during use of the well logging tool.

In an attempt to produce a more consistent static magnetic field, manufacturers attempt to control the overall static magnetic field by adding shims to the magnetic material package. These shims, coupled with removal of magnetic material, for example, can influence the overall static magnetic field delivered by the nuclear magnetic resonance tool. Problems with this type of arrangement abound. Careful mapping and determination of the strength of magnets being installed in the tool must be accomplished in order to determine the field strength. Placement of shims inside a tool, additionally, takes up vital space in the inside of the tool that could be used for more practical purposes.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter. A method to produce a magnet arrangement, the method having steps of selecting a depth of investigation to be achieved by a downhole tool, identifying a desired magnetic field strength at the depth of investigation, producing a set of magnets to be incorporated into the downhole tool, sorting the set of magnets based on a quality of each of the magnets and optimizing the set of magnets such that the quality of each of the magnets results, when arranged, in the desired magnetic field strength at the depth of investigation and wherein the optimizing minimizes a cost function of the set of magnets produced.

BRIEF DESCRIPTION OF THE DRAWINGS

The patent or application file contains at least one drawing executed in color. Copies of this patent or patent application publication with color drawing(s) will be provided by the Office upon request and payment of the necessary fee. In the drawings, sizes, shapes, and relative positions of elements are not drawn to scale. For example, the shapes of various elements and angles are not drawn to scale, and some of these elements may have been arbitrarily enlarged and positioned to improve drawing legibility.

DETAILED DESCRIPTION

An aspect of this disclosure is to reduce the wasted magnet material (hence magnet cost) to maintain the consistency in fabricating magnets for Nuclear Magnetic Resonance (NMR) tools. This aspect is realized by optimizing the arrangement of non-perfect magnet segments, so that the combination of the segments produces sufficiently homogeneous magnetic fields that meets various NMR requirements. This is accomplished without using additional shimming materials that use limited space on an NMR sensor.

The sensor of the Nuclear Magnetic Resonance (NMR) well logging tools consists of permanent magnet(s) and antenna(e) to project a static magnetic field ($B_0$) and oscillating magnetic field ($B_1$) into a formation surrounding a wellbore. A resulting tool sensitive region is determined by a resonance frequency of nuclear spins, which is proportional to the local static magnetic field $B_0$ strength, and the frequency bandwidth of an excitation signal, which is proportional to local oscillating magnetic field $B_1$ strength as described in FIG. 1.

Figure 1:
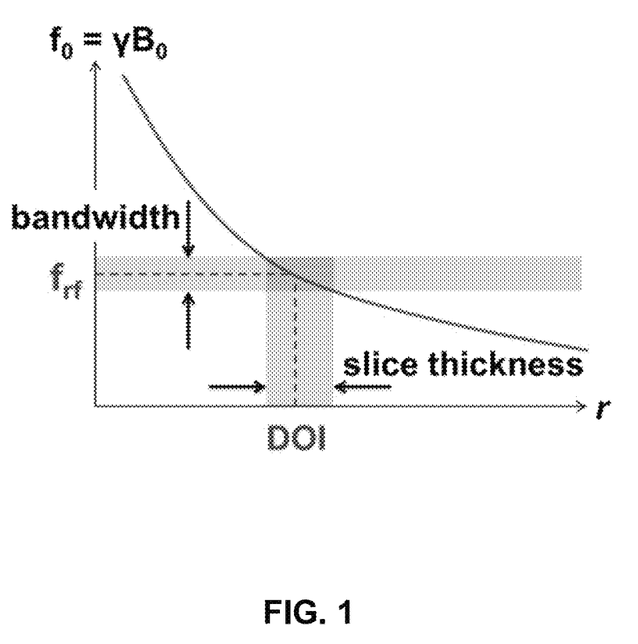
FIG. 1 is a graph of a relationship between excitation pulse frequency and depth of investigation (in length units).

As provided in FIG. 1, a relationship between the static magnetic field, $B_0$, oscillating magnetic field, $B_1$, and the sensitive region, as described above, is illustrated. The resonance frequency of nuclear magnetization, $f_0$, is proportional to local static magnetic field strength $B_0$ through a coefficient $\gamma$. For an excitation pulse of frequency $f_{rf}$, the depth of investigation (DOI) is determined by the location where the equation $f_{rf}=f_0=\gamma B_0$ is satisfied. In addition, thickness of the sensitive region is determined by the homogeneity of the static magnetic field strength $B_0$ and the bandwidth of the excitation pulse, which is proportional to the pulsed magnetic field strength $B_1$.

If the nominal static magnetic field strength $B_0$ deviates from a target value, then the depth of investigation (DOI) will shift closer to or further from the tool, resulting in potential signals coming from unwanted regions (e.g., the borehole). If static magnetic field strength $B_0$ homogeneity is compromised, then the resonance frequency also spreads across the region of interest, and only a fraction of the regions will be excited by the oscillating magnetic field strength $B_1$ of a given bandwidth. The result is a reduced NMR signal. Nominal static magnetic field strength $B_0$ and the homogeneity of the static magnetic field strength $B_0$ around the region of interest are one of the most important properties of an NMR sensor.

Each NMR well logging tool has a unique operating profile and associated requirements for the sensitive region. For example, wireline tools often require an elongated sensitive region along a tool axis to scan the formation at relatively high speed (up to 3,600 ft/hour). Logging While Drilling (LWD) tools, meanwhile, require an axisymmetric sensitive region to conduct NMR measurements under rotating conditions. Efforts have been made to generate specific static magnetic field strength $B_0$ and oscillating magnetic field strength $B_1$ distributions to satisfy the above requirements.

To realize specific static magnetic field strength $B_0$ distribution, the magnet is usually composed of multiple (from 10s to 100s) segments, each of which is magnetized in a pre-defined direction. The tolerances of those segments, however, are limited by the complicated manufacturing process. First, a mixture of rare earth magnetic materials, such as Samarium (Sm) and Cobalt (Co), and other ingredients are melted in a furnace to obtain a cast ingot. The ingot is then crushed, pulverized, and milled into small particles of several micrometers. The obtained alloy particles are compressed in a die to be formed into magnet blocks while aligning the orientations with applied magnetic field. The magnet block is then sintered, heat treated, magnetized, and shaped. If shaping needs to happen after magnetization, a special technique, such as Electric Discharge Machining (EDM), shall be used to avoid mechanical damage.

Figure 2:
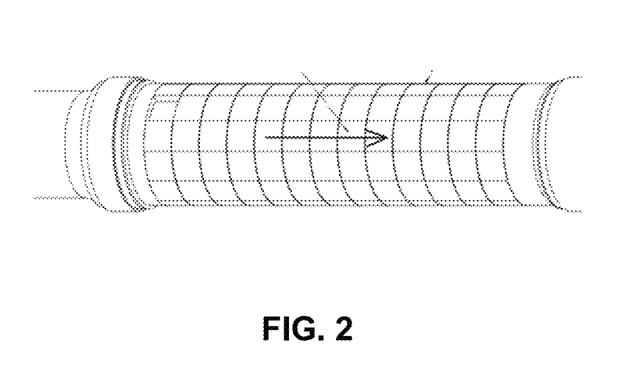
FIG. 2 is a side view of a construction of a cylindrical magnet array of a set of magnet segments, wherein each segment has a nominal direction parallel to the cylinder axis.
Figure 3:
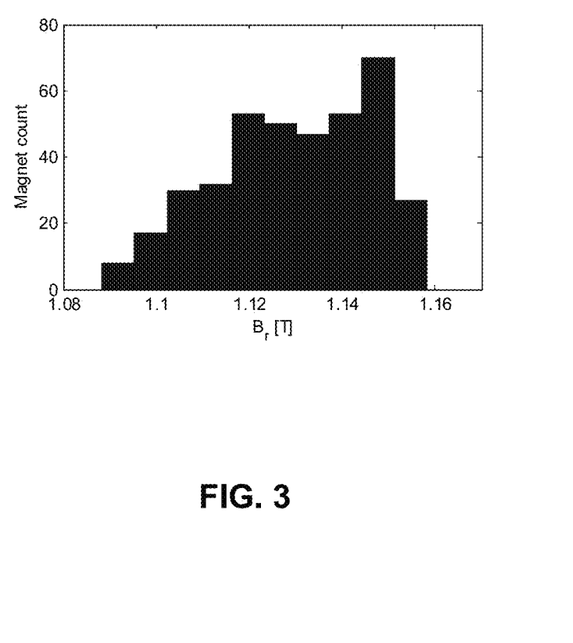
FIG. 3 is a distribution graph of remnant magnetization for 387 magnet segments.

The above process introduces variations both in the strength and magnetizing direction. As a result, an ensemble of magnet segments exhibits certain distribution, which varies from batch to batch. FIG. 2 shows an example of a cylindrical magnet array that consists of 168 segments. Each segment has a nominal magnetizing direction parallel to the cylinder axis. FIG. 3 shows the remnant magnetization ($B_r$) of 387 segments prepared to build a magnet array. The material (SmCo R32H) is designed to have $B_r$=1.12~1.20 T, but the actual distribution is shifted towards the lower end in this particular example. If these segments are randomly arranged on a cylinder, the resulting static magnetic field strength $B_0$ will be distorted and lose axisymmetric properties as provided in FIG. 4. This will cause inconsistent signal amplitude in LWD operation. Furthermore, deviation of the static magnetic field strength $B_0$ causes the shift of the DOI from the target location.

Referring to FIG. 2, the construction of a cylindrical magnet array is illustrated wherein the array consists of a set of magnet segments. Each segment has a nominal magnetizing direction parallel to the cylinder axis as indicated by the arrow.

Referring to FIG. 3, a distribution of remnant magnetization ($B_r$) for 387 magnet segments is illustrated. The material (SmCo R32H) is supposed to have $B_r$=1.12~1.20 T.

Figure 4:
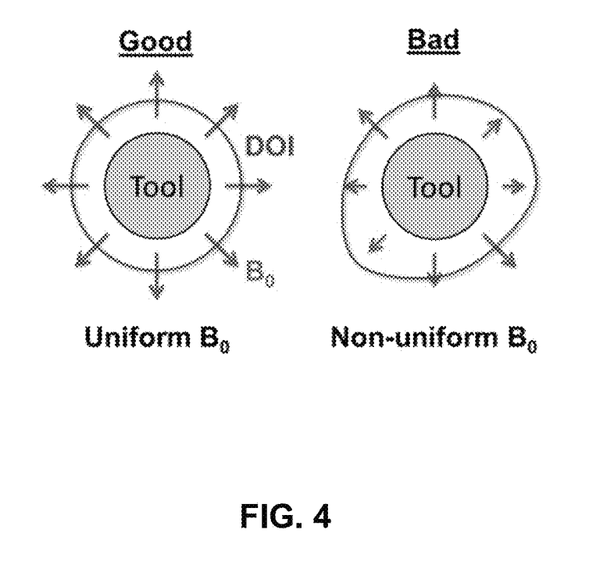
FIG. 4 is a comparison graph of a tool with a uniform static magnetic field vs. a non-uniform static magnetic field.

Referring to FIG. 4, a shape of the sensitive region dictated by static magnetic field strength $B_0$ distribution is illustrated. If the static magnetic field strength $B_0$ is uniform around the tool, then the DOI will be uniform as well as illustrated on the left. If the static magnetic field strength $B_0$ is not uniform, then the DOI is distorted and the NMR signal will be compromised in the rotating operation as illustrated on the right. This requires static magnetic field strength $B_0$ consistency within a tool and among multiple tools.

Figure 5:
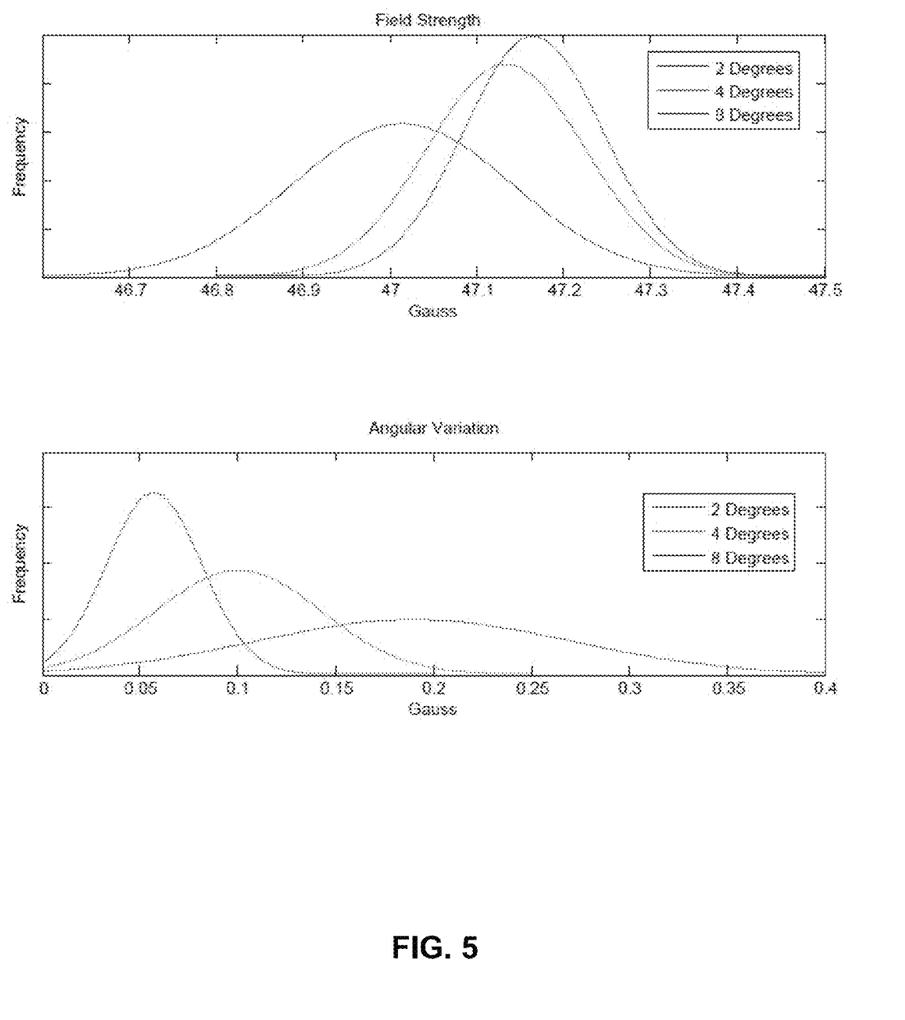
FIG. 5 is a graph of cylindrical magnet array properties when constructed from a set of magnet segments with specific angular offset distributions.

To avoid such tool performance degradation, stringent pass/fail criteria are imposed on individual segments assuming the worst case scenario (e.g., all segments are tilted in the same way). For example, FIG. 5 shows the likelihood of magnet properties when segments of certain tolerance are randomly distributed on a cylinder. For this particular example, the angular offset is within two (2) degrees to satisfy tool requirements (i.e., 47.5±0.5 G for field strength to maintain the consistency of DOI, and 0.2 G for Angular Variation to maintain the uniformity of cylindrical sensitive region). Segments beyond +/−2 degree tolerance must be discarded. This severely brings down the yield rate of the manufacturing process and thus is reflected in the high cost of magnet arrays.

Referring to FIG. 5, a likelihood of cylindrical magnet array properties when constructed from a set of magnet segments with specific angular offsets is illustrated. Each distribution represents the histogram of 5,000 magnet array implemented randomly.

One aspect described herein is to reduce the wasted magnet material (hence magnet cost) by optimizing the arrangement of non-perfect magnet segments, so that the combination of the segments produces sufficiently homogeneous static magnetic field strength $B_0$ that meets various NMR requirements. This shall be done without using additional shimming materials that eat up limited space on an NMR sensor.

The optimization involves the evaluation of a magnetic field produced by a set of magnet segments. When the point of interest is at a large distance from the source dipoles, the magnetic field may be approximated by a dipole field. The magnetic field flux density at point r is given by the below equation:

$$B = \frac{\mu_o}{4\pi}\left[\frac{3r(m \cdot r)}{R^5} - \frac{m}{R^3}\right]$$

where m is magnetic moment, R is the distance between the source m and point r, and $\mu_0$ is the permeability of free space. The total field may be obtained by integrating the contribution of magnetic dipoles that represent each segment. Although such a simple dipole model is fast and convenient in optimization process that involves many iterations, Finite Element Analysis (FEA) or any other methods may also be used to calculate the magnetic field.

The magnetic dipole moment is a vector that has the magnitude and direction, both of which show variations in real-world magnets. The goal of this optimization is to find a set of m, within which small local variations cancel out with each other. Then the resulting static magnetic field B will have a global distribution that is sufficiently uniform over the region of interest.

A set of magnet segments may be sorted out based on the quality prior to the arrangement optimization. The example of quality includes the magnetization strength and the angular offset. The closer the magnetization is to the pre-determined optimal value, the better the magnet. Also, the smaller the offset angle is, the better the magnet. Once the magnets are sorted, the magnets are evenly split between multiple magnet assemblies, so that each assembly has a distribution of good and poor segments.

The optimization may be implemented to minimize the cost function that represents the quality of the magnet assembly. One example of magnet quality is the deviation from the target field value. By using multiple points, field homogeneity may be defined in the region of interest. For example, for a cylindrical magnet given in FIG. 2, the variations of magnetic field in both the axial and angular directions may be minimized in a single run of optimization. Other types of magnet array may have sensitive regions of different shapes, but similar criteria may be defined for optimization.

There are multiple algorithms to realize the optimization. The easiest but most inefficient way is the Monte-Carlo method, where the combinations of magnet segments are randomly chosen to compare the performance of resulting magnet array. For example, for the cylindrical magnet given in FIG. 2 made out of magnet segments given in FIG. 3, the smallest angular variation was found to be 0.0085 G after 10,000 iterations, which is one order of magnitude better than the average value 0.053 G obtained in the same iterations. The drawback of this approach is the coverage of the solution space; in the above example, there are $_{387}P_{168}$ candidate solutions (i.e., select 168 segments out of 387 segments and assemble them in a particular order) to be evaluated, which is a large number and will, for most purposes, not be thoroughly investigated. This would result in sub-optimal results. For the purpose of the disclosed aspects, sub-optimal solutions are acceptable as long as the static magnetic field strength $B_0$ variations are small enough compared to the errors introduced by other factors (e.g., mechanical tolerance in locating magnet segments on a cylindrical collar).

To obtain similar or even better results, a more efficient method is to evolve candidate solutions based on the result of the previous iteration. This will allow the finding of (quasi-)optimal solution(s) without evaluating all the candidates. The examples of optimization algorithms suitable for combinational optimization problem like this includes, but not limited to, Genetic Algorithm, Simulated Annealing method, Taboo Search method, Simulated Evolution method, Stochastic Evolution method, and Hybrid method (i.e., a combination of them), among others.

Figure 6:
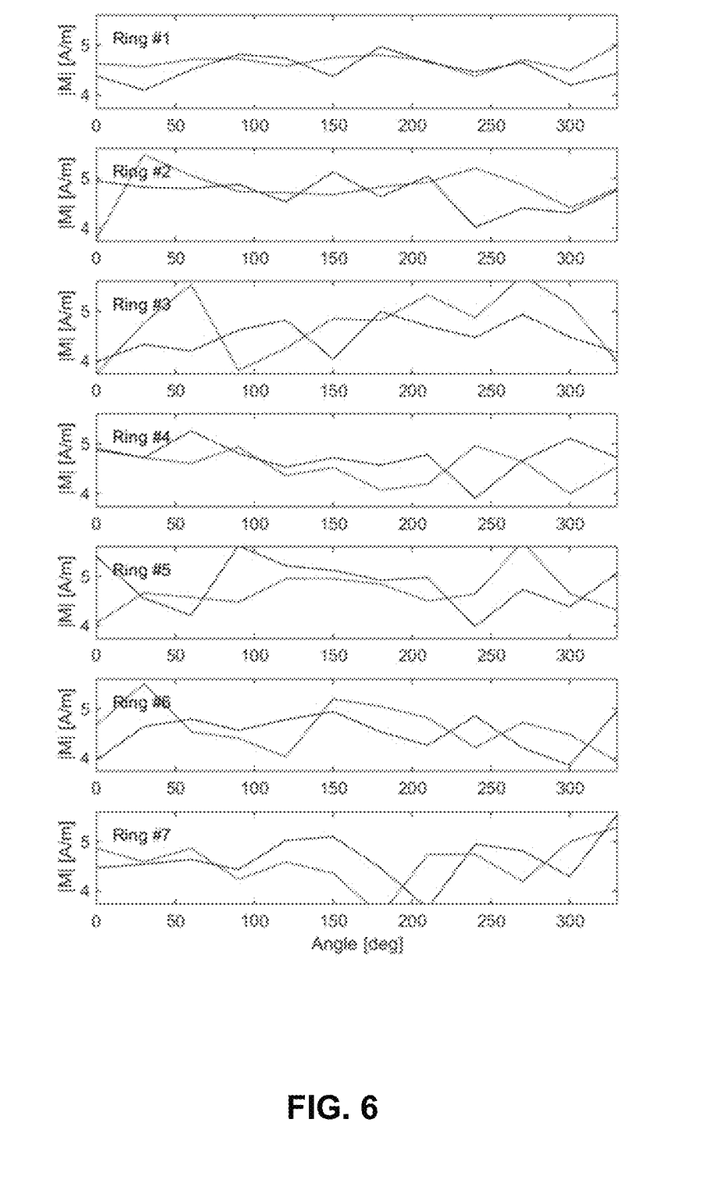
FIG. 6 is a graph of optimized segment arrangements for seven inner rings of cylindrical arrays.

Regardless of the algorithms being used, the optimization process will ensure segment configuration that generates a static magnetic field $B_0$ with the smallest deviations from the target distribution. For example, FIG. 6 shows the optimized segment arrangement for the inner 7 rings of cylindrical magnet arrays. The horizontal axis is the segment position on a collar specified in angle, and the vertical axis is the segment strength. Designated lines represent the result for a pair of magnet arrays facing with each other. It can be seen that, at some point, a strong segment in inner ring is compensated by a weaker segment in outer ring. Also, good segments were located on the inner most ring, while the bad segments were left away in the outer rings (i.e., far from the sensitive region).

Referring to FIG. 6, an optimized segment arrangement for the inner 7 rings of cylindrical magnet arrays from FIG. 2 is displayed. The optimization process will typically place the segments of good quality close to the sensitive region, while the process will move ones with non-optimal quality to the far end of the spectrum. The optimization process will typically place a segment with positive variation next to the one with negative variation, so that the local variations cancel out when the field point is at a large distance.

Figure 7A:
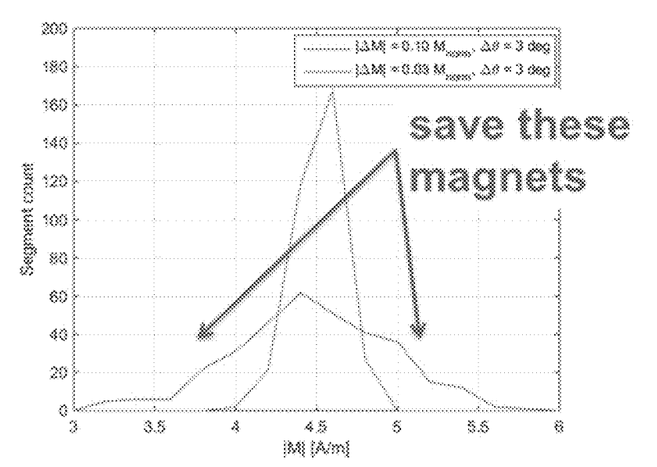
FIG. 7A is example of segment distribution of magnets to be used for downhole tools.
Figure 7B:
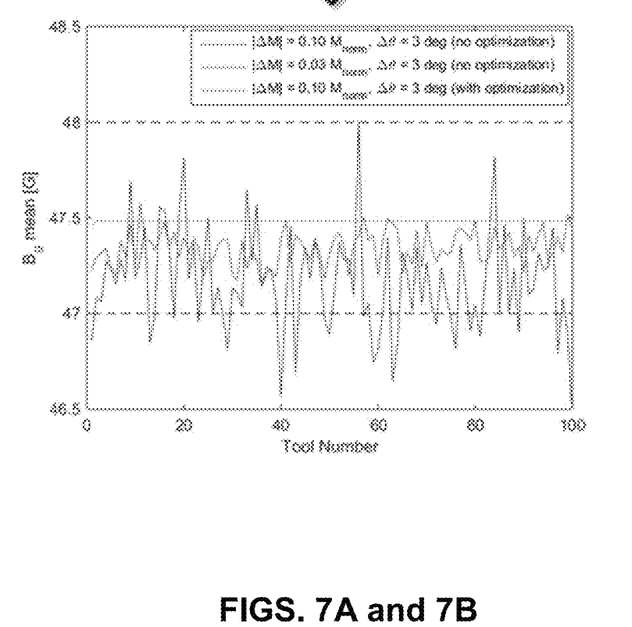
FIG. 7B is a resulting static magnetic field $B_0$ at a point of interest from the segment distribution of FIG. 7A.

Referring to FIG. 7, a resulting static magnetic field $B_0$ is illustrated. The noted lines represent the distribution of segment properties with loose and tightened tolerances. If 100 magnets are built from a set of segments specified, the resulting magnetic field can be higher or lower than the target value, and there is a significant chance to receive a magnet that is out of the spec. If optimization is implemented, the same distribution delivers magnets, which are consistently around the target value, 47.5 G. In other words, the optimization saves the bad segments that are otherwise discarded. Considering the high value of rare-earth magnet materials, the reduction of wasted materials has a significant impact on the magnet cost.

As demonstrated above, the optimization process provides consistent static magnetic field $B_0$ out of a sub-optimal set of magnet segments. This will contribute to maintain the DOI for fixed operating frequency. The same technique may be used to reduce the variation of operating frequency (hence reduce the need for antenna/electronics adjustment) for the fixed target DOI.

Referring to FIGS. 7A and 7B an example of segment distribution (top) and resulting $B_0$ field at a point of interest (bottom) are illustrated. In the top figure, the blue and red lines represent the segment properties with loose and tightened tolerances. If 100 magnets are built from such segments, the resulting static magnetic field can be higher or lower than the target value, and there is a significant chance to receive a magnet that is out of the spec (bottom). However, if the optimization is implemented, the same blue distribution delivers the green line, which is consistently around the target value, 47.5 G. The optimization will save the bad segments that are otherwise discarded.

In one example embodiment, a method to produce a magnet arrangement, comprising selecting a depth of investigation to be achieved by a downhole tool, identifying a desired magnetic field strength at the depth of investigation, producing a set of magnets to be incorporated into the downhole tool, sorting the set of magnets based on a quality of each of the magnets and optimizing the set of magnets such that the quality of each of the magnets results, when arranged, in the desired magnetic field strength at the depth of investigation and wherein the optimizing minimizes a cost function of the set of magnets produced.

In a further example embodiment, the method may be accomplished wherein the identifying the desired magnetic field strength at the depth of investigation is approximated by a dipole field.

In a further example embodiment, the method may be accomplished wherein a magnetic flux density at a point r for the depth of investigation is calculated as:

$$B = \frac{\mu_o}{4\pi}\left[\frac{3r(m \cdot r)}{R^5} - \frac{m}{R^3}\right]$$

where m is a magnetic moment, R is the distance between a source m and point r, and $\mu_0$ is the permeability of free space.

In a further example embodiment, the method may be accomplished wherein the quality is a magnetization strength.

In a further example embodiment, the method may be accomplished wherein the quality is an angular offset.

In a further example embodiment, the method may be accomplished wherein the quality is both a magnetization strength and an angular offset.

In a further example embodiment, the method may further comprising splitting the set of magnets between multiple magnet assemblies being constructed.

In a further example embodiment, the method may be accomplished wherein the optimizing the set of magnets is performed through a Monte Carlo method.

In a further example embodiment, the method may be accomplished wherein the optimizing the set of magnets is performed through at least one of a genetic algorithm, a simulated annealing method, a taboo search method, a simulated evolution method and a stochastic evolution method.

A few example embodiments have been described in detail above; however, those skilled in the art will readily appreciate that many modifications are possible in the example embodiments without materially departing from the scope of the present disclosure or the appended claims. Accordingly, such modifications are intended to be included in the scope of this disclosure. Likewise, while the disclosure herein contains many specifics, these specifics should not be construed as limiting the scope of the disclosure or of any of the appended claims, but merely as providing information pertinent to one or more specific embodiments that may fall within the scope of the disclosure and the appended claims. Any described features from the various embodiments disclosed may be employed in combination. In addition, other embodiments of the present disclosure may also be devised which lie within the scope of the disclosure and the appended claims. Additions, deletions and modifications to the embodiments that fall within the meaning and scopes of the claims are to be embraced by the claims.

Certain embodiments and features may have been described using a set of numerical upper limits and a set of numerical lower limits. It should be appreciated that ranges including the combination of any two values, e.g., the combination of any lower value with any upper value, the combination of any two lower values, or the combination of any two upper values are contemplated. Certain lower limits, upper limits and ranges may appear in one or more claims below. Numerical values are "about" or "approximately" the indicated value, and take into account experimental error, tolerances in manufacturing or operational processes, and other variations that would be expected by a person having ordinary skill in the art.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include other possible embodiments along with the full scope of equivalents to which such claims are entitled. Accordingly, the claims are not limited by the disclosure.

What is claimed is:

1. A method for fabricating a magnet on a nuclear magnetic resonance logging tool, the method comprising:
   identifying a desired magnetic field strength at a predetermined depth of investigation about the logging tool;
   receiving a set of magnet segments configured for deployment on the logging tool in a magnet arrangement comprising a plurality of rings of the magnet segments which make up a cylindrical magnet array on the logging tool, each of the magnet segments having a corresponding magnetic strength and angular offset;
   obtaining a plurality of magnet arrangement solutions of selected ones of the magnet segments arranged in the cylindrical magnet array on the logging tool wherein each selected magnet segment is deployed in a unique location on the logging tool;
   processing the magnetic strength and angular offset of each selected magnet segment and the unique location of each selected magnet segment arranged in the cylindrical magnet array of each of the obtained magnet arrangement solutions to compute corresponding magnetic field strength solutions at the predetermined depth of investigation for each of said plurality of magnet arrangement solutions;
   selecting one of said magnet arrangement solutions that minimizes a difference between the magnetic field strength solution and the desired magnetic field strength at the predetermined depth of investigation;
   deploying the selected magnet segments on the logging tool according to said selected magnet arrangement solution to fabricate the magnet.

2. The method according to claim 1, wherein said processing comprises computing the magnetic field strength solutions by integrating the contribution of magnetic dipoles that represent each of the magnet segments.

3. The method according to claim 2, wherein a magnetic flux density at a point r for the depth of investigation is calculated for each of the magnet segments as:

$$B = \frac{\mu_o}{4\pi} \left[ \frac{3r(m \cdot r)}{R^5} - \frac{m}{R^3} \right]$$

where m is a magnetic moment, R is a distance between a source magnetic moment m and the point r, and $\mu_0$ is the permeability of free space.

4. The method according to claim 1, wherein said plurality of magnet arrangement solutions are randomly chosen using a Monte Carlo method.

5. The method according to claim 1, wherein said plurality of magnet arrangement solutions are obtained by using at least one of a genetic algorithm, a simulated annealing method, a taboo search method, a simulated evolution method and a stochastic evolution method.

6. The method of claim 1, wherein:
   said processing further comprises processing the magnetic strength and angular offset of each selected magnet segment and the unique location of each selected magnet segment to compute corresponding angular variations of the magnetic field strength solutions at the predetermined depth of investigation for each of said plurality of magnet arrangement solutions; and
   said selecting comprises selecting said magnet arrangement solution that further minimizes the angular variation in the magnetic field strength solution at the depth of investigation.

7. The method of claim 1, wherein:

said processing further comprises processing the magnetic strength and angular offset of each selected magnet segment and the unique location of each selected magnet segment to compute corresponding axial variations of the magnetic field strength solutions at the predetermined depth of investigation for each of said plurality of magnet arrangement solutions; and said selecting comprises selecting said magnet arrangement solution that further minimizes the axial variation in the magnetic field strength solution at the depth of investigation.

8. The method of claim 1, wherein said receiving the set of magnet segments comprises (i) producing the set of magnet segments and (ii) obtaining the magnetic strength and angular offset of each of the magnet segments.

9. The method of claim 1, wherein obtaining the plurality of magnet arrangement solutions comprises:

sorting the set of magnet segments into good segments and poor segments based on said magnetic strengths and angular offsets, wherein the good segments include the magnet segments that meet predetermined magnetic strength and angular offset criteria and the poor segments include the magnet segments that fail to meet the predetermined magnetic strength and angular offset criteria; and obtaining the plurality of magnet arrangement solutions such that each magnet arrangement solution includes a distribution of the good segments and the poor segments.

10. The method of claim 9, wherein:

wherein the plurality of rings of the magnet segments of the cylindrical magnet array on the logging tool include inner rings and outer rings, wherein the good segments are located in the inner rings and the bad segments are located in the outer rings.

* * * * *